(12) United States Patent
Elbrecht et al.

(10) Patent No.: US 6,682,524 B1
(45) Date of Patent: Jan. 27, 2004

(54) DERMATOLOGICAL HAND PIECE

(75) Inventors: Jens Elbrecht, Jena (DE); Juergen Kuehnert, Jena (DE); Bernhard Seitz, Jenapriessnitz (DE); Gabriele Zimmermann, Jena (DE)

(73) Assignee: Asclepion Laser Technologies GmbH, Jena (DE)

( * ) Notice: Subject to any disclaimer, the term of this patent is extended or adjusted under 35 U.S.C. 154(b) by 0 days.

(21) Appl. No.: 09/831,693

(22) PCT Filed: Aug. 11, 1999

(86) PCT No.: PCT/EP99/05888

§ 371 (c)(1),
(2), (4) Date: Aug. 27, 2001

(87) PCT Pub. No.: WO00/28910

PCT Pub. Date: May 25, 2000

(30) Foreign Application Priority Data

Nov. 12, 1998 (DE) .......................... 198 52 948

(51) Int. Cl.[7] .............................. A61B 18/20
(52) U.S. Cl. .............................. 606/9; 606/13
(58) Field of Search ................. 606/9–10, 13; 607/88, 89

(56) References Cited

U.S. PATENT DOCUMENTS

| 3,816,160 A | * | 6/1974 | Moore ...................... 359/652 |
| 4,733,660 A | * | 3/1988 | Itzkan ........................... 606/9 |
| 5,057,104 A |   | 10/1991 | Chess |
| 5,486,172 A | * | 1/1996 | Chess ........................... 606/10 |
| 5,658,275 A | * | 8/1997 | Saadat ............................ 606/9 |
| 5,735,844 A | * | 4/1998 | Anderson et al. ............... 606/9 |
| 5,738,681 A |   | 4/1998 | Shimizu |
| 5,830,208 A | * | 11/1998 | Muller .......................... 606/9 |
| 5,968,034 A | * | 10/1999 | Fullmer et al. ................ 606/9 |
| RE36,634 E | * | 3/2000 | Ghaffari ........................ 606/9 |
| 6,235,015 B1 | * | 5/2001 | Mead et al. ................... 606/9 |
| 6,273,884 B1 | * | 8/2001 | Altshuler et al. .............. 606/9 |
| 6,383,176 B1 |   | 5/2002 | Connors et al. |

FOREIGN PATENT DOCUMENTS

| EP | 0 783 904 | 7/1997 |
| EP | 0 827 716 | 3/1998 |
| WO | WO 91/04829 | 4/1991 |
| WO | WO 95/18984 | 7/1995 |
| WO | WO 98/51235 | 11/1998 |
| WO | WO 98/52481 | 11/1998 |

* cited by examiner

*Primary Examiner*—Roy D. Gibson
*Assistant Examiner*—Henry M. Johnson
(74) *Attorney, Agent, or Firm*—Reed Smith LLP

(57) ABSTRACT

A dermatological handpiece by which a laser beam is directed to the surface of a selected skin area for purposes of a cosmetic treatment and the skin area is subjected to the action of the laser beam. A method is also disclosed for the cosmetic treatment of skin surfaces during the operation of this handpiece. A handpiece of the type described above is outfitted with a device for moderating the temperature of the skin surfaces on which the laser beam acted immediately beforehand and/or is to be subjected to the action of the laser beam immediately following the temperature moderation. The handpiece is further provided with elements for influencing the laser beam cross section with respect to shape, dimensioning and intensity distribution.

34 Claims, 5 Drawing Sheets

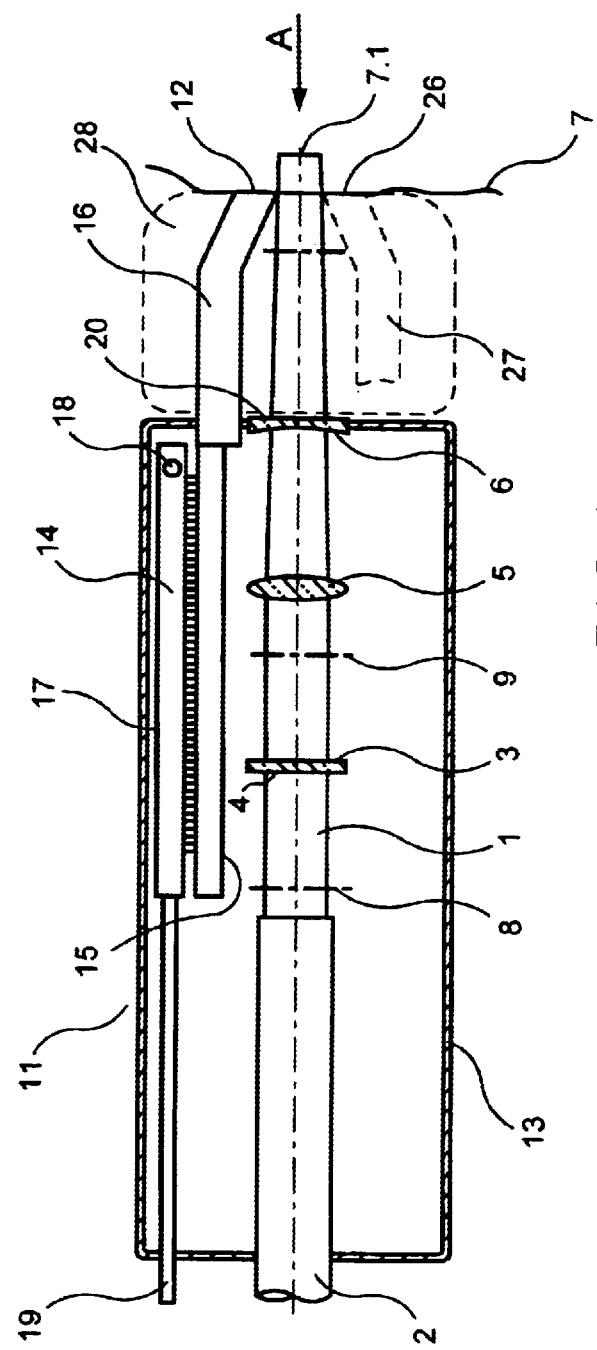
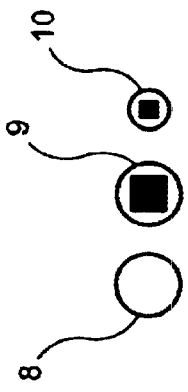
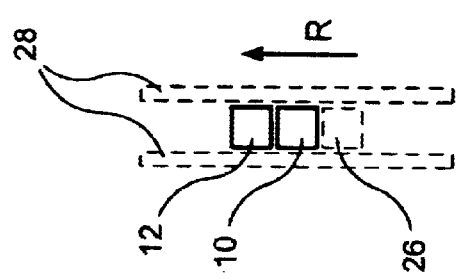

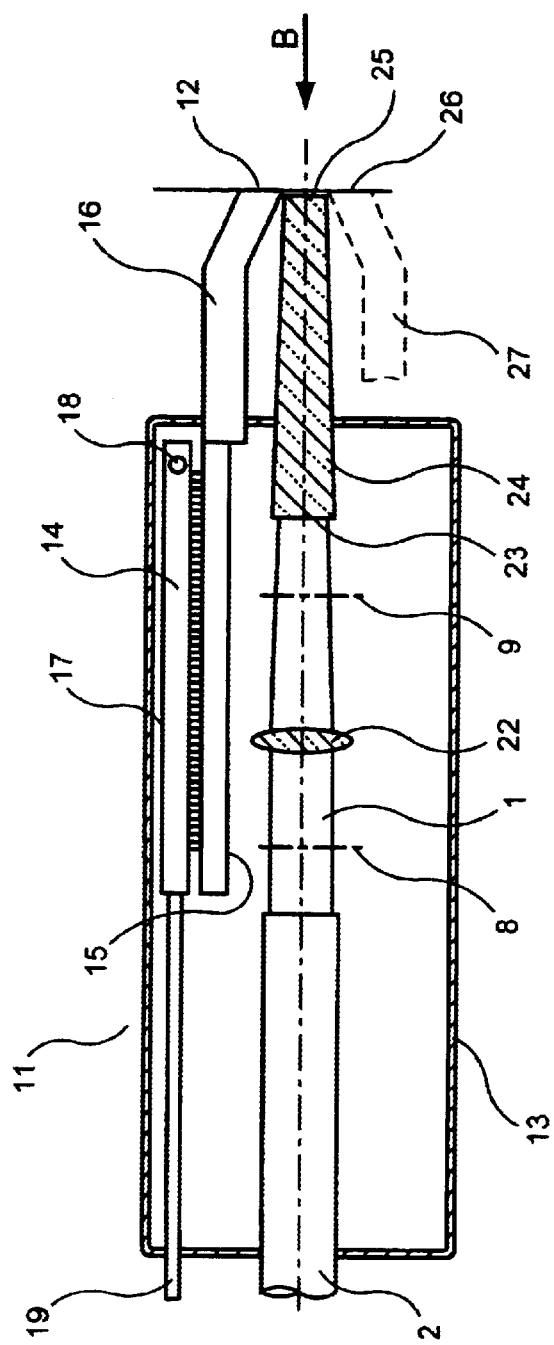
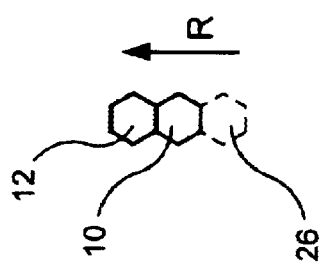
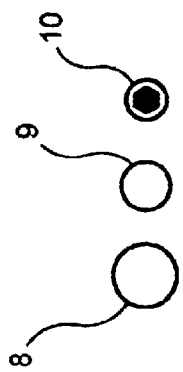
FIG. 4
FIG. 5
FIG. 6

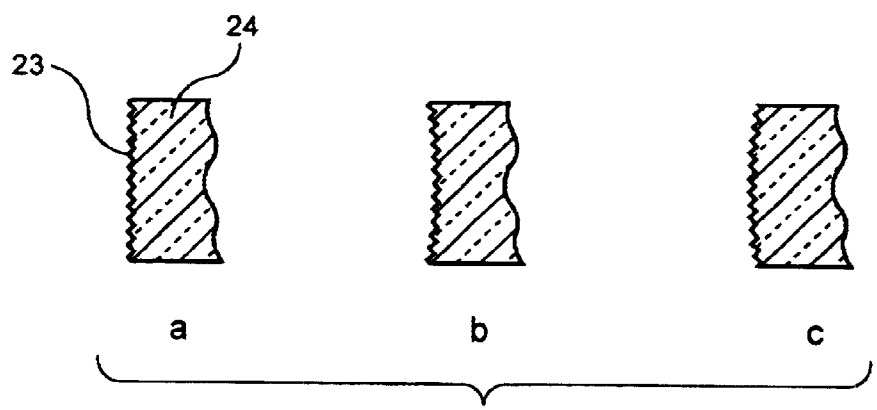
F I G. 10
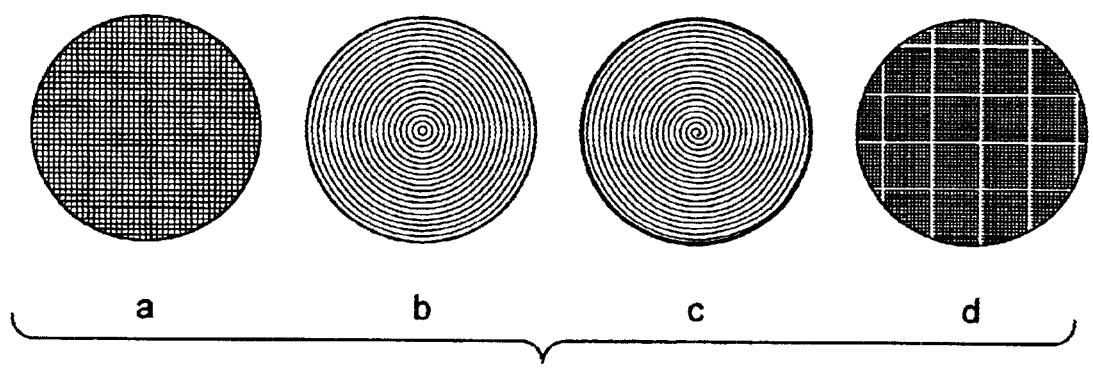
F I G. 11
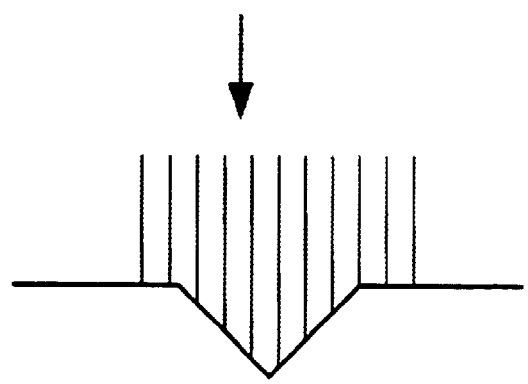
F I G. 12

DERMATOLOGICAL HAND PIECE

CROSS-REFERENCE TO RELATED APPLICATIONS

This application claims priority of German Application No. 198 52 948.1, filed Nov. 12, 1998 and International Application No. PCT/EP99/05888, filed Aug. 11, 1999, the complete disclosure of which is hereby incorporated by reference.

BACKGROUND OF THE INVENTION a) Field of the Invention

The invention is directed to a handpiece for cosmetic treatment of skin surfaces, by which a laser beam is directed to a selected skin area which is subjected to the action of the laser beam. The invention is further directed to a method for cosmetic treatment of skin surfaces while operating a handpiece of the type mentioned above.

b) Description of the Related Art

Lasers are currently used the world over for cosmetic treatment of the skin, primarily of vascular and pigmented lesions, e.g., for removal of port-wine stains and tattoos, for skin resurfacing and also for hair removal. Usually, short laser pulses with a pulse duration in the nanosecond to millisecond range are introduced into the tissue for this purpose. Treatments of this kind serve primarily to improve the quality of life of the patient and are generally of a cosmetic nature.

The equipment for carrying out such treatments essentially comprises a laser radiation source and a handpiece which is used for directing the beam emitted by the laser radiation source onto the skin area to be treated.

In order to achieve a lightweight construction of the handpiece and thus to enable the freest possible handling of the handpiece, the laser radiation source and handpiece are constructed as separate subassemblies, and the transmission of laser radiation from the radiation source to the handpiece is carried out by means of a movable beam guidance device. The beam guidance unit can be formed of a plurality of rigid transmission members interconnected by joints or may also be constructed as a flexible fiber optic system or in some other way.

The handpiece has an in-coupling element at the transition from the beam guidance unit and an emission surface for the laser beam is provided at the end of the handpiece to be directed to the skin. Often, there is a spacer which fixes the working plane and accordingly ensures that the cross section and intensity of the applied laser beam in the working plane correspond to the selected parameters.

For many dermatological applications, it is advantageous to cool the outer skin layers in order to prevent laser radiation damage. Various methods and devices are known for this purpose.

For example, it is common to apply cooling gel to the surface to be treated or the surface to be treated is cooled by a spray. However, it is difficult to influence the temperature on the skin and in the layers located immediately below it in such a way that the desired treatment effect is achieved on the one hand and laser radiation damage to the epidermis is extensively prevented on the other hand. A further disadvantage consists in that a local uniform cooling is not guaranteed.

U.S. Pat. No. 5,057,104 describes a method and a device for treating cutaneous vascular lesions in which the laser beam is guided by a stationary cooling container communicating with the skin segment to be treated. In this way, heat is removed from the skin area during treatment.

U.S. Pat. No. 5,735,844 discloses a device for hair removal in which an optically transparent lens through which the laser beam is directed onto the skin area to be treated is brought into contact with a cooling unit as well as with the skin. In so doing, the lens also removes heat during the treatment of the skin area in question, as was described above.

In the devices mentioned above, the large space requirement caused by the dimensions of the cooling means placed on the skin has proved disadvantageous. This constitutes a hindrance when treating small surfaces. Further, the heat conductivity of the available materials which are transparent for laser radiation is comparatively poor so that fast, optimal cooling cannot be achieved.

Another substantial disadvantage consists in that when positioning the outlet optics for the laser beam and the cooling device it is initially necessary to wait before irradiating with laser energy until the skin site to be treated has cooled optimally. This is particularly disadvantageous when treating a larger skin surface on which the laser radiation must be introduced in several adjacent skin areas. The treatment period is relatively long due to the fact that a dwell or holding time is required for cooling for each of these skin areas first and the laser irradiation can take place only then.

Also, post-treatment of the affected skin portions by means of temperature control is impossible with the known handpieces.

OBJECT AND SUMMARY OF THE INVENTION

Based on this prior art, it is the primary object of the invention to further develop a handpiece for cosmetic treatment of skin areas by means of laser radiation in such a way that a more efficient treatment is ensured while protecting the skin as far as possible.

According to the invention, a handpiece of the type described above is outfitted with a device for moderating the temperature of the selected skin surface before and/or after its treatment. Accordingly, it is possible for a skin surface to be cooled or heated, as required, immediately before treatment with laser radiation and also, if required, to subject it to post-treatment by supplying or removing heat.

In a handpiece by which the laser beam is directed successively to individual skin areas corresponding to the laser beam cross section and covering the selected skin surface in its entirety, there is at least one temperature-moderated contact surface laterally adjacent to the exiting laser beam. According to the invention, the distance between the laser beam and a contact surface of the type mentioned above is dimensioned in such a way that a first skin area on which the laser beam was previously directed and on which the laser beam has just acted is in contact with the contact surface at the same time that the laser beam is directed to a second skin area. Alternatively or in addition, there can be another contact surface whose distance from the laser beam is so dimensioned that it is in contact with a third skin area on which the laser beam is to act in the next step (while the laser beam is still simultaneously directed to the second skin area and the first skin area is still in contact with the first contact surface).

Similarly, additional contact locations can be provided at the handpiece and, while the laser beam is directed to and acts on the second skin area, these other contact locations are in contact with other previously treated skin areas and/or with other skin areas to be treated subsequently by means of moderating temperature.

In other words, the contact surfaces are positioned at the handpiece in relation to the laser beam in such a way that while the laser beam acts upon a skin area, at least one other skin area on which the laser beam had acted previously (before moving the handpiece) and/or on which the laser beam is to act subsequently (after the handpiece is moved) is in contact with a contact surface. In this way, the temperature of the individual skin areas is moderated in immediate preparation for the laser beam action and/or for purposes of post-treatment. The handpiece can therefore be advanced progressively from one skin area to another without delay.

In construction variants, the dimensions of the contact surface may be smaller or larger than the dimensions of the laser beam cross section. In this way, it is possible, for example, to moderate the temperature of a larger surface portion before treatment, so that only surface portions whose temperature has already been moderated are subjected to the action of the laser beam and safety is increased. Moderating the temperature of a surface that is smaller in comparison to the laser beam cross section can serve for a gentler treatment of certain skin areas.

According to the invention, the at least one contact surface is connected with a cooling unit and/or heating unit in a heat-conducting manner. Preferably, a cooling unit is provided. This cooling unit may be constructed, for example, as a Peltier element whose cool side communicates in a heat-conducting manner with the contact surface, the heat removed from the skin area being carried away from its warm side via a medium which circulates in a cooling circuit.

Alternatively, it is also possible that the contact surface is made to communicate in a heat-conducting manner with an expanding, and therefore cooling, gas, e.g., nitrogen or carbon dioxide, while this contact surface rests on the skin area whose temperature is to be moderated beforehand.

In a particularly preferred construction, a temperature sensor is provided at the handpiece and communicates with the contact surface and/or with the skin area which is selected for treatment and whose temperature is to be moderated. It is determined by means of this temperature sensor whether or not the skin area has reached the temperature that is required for treatment and that is a precondition for successful treatment. The output signal of the temperature sensor can be used as a switch-on signal or control signal for the cooling and/or heating unit. In this way, it is possible to further increase or reduce the temperature of the selected skin area, as needed.

In another construction, the laser beam cross section is surrounded by an annular surface which rests on the skin area selected for treatment. By means of this annular surface, the skin area can be exposed to a pressure which favors successful treatment because the thickness of the epidermis is reduced by the area pressure between the annular surface and the skin, so that the laser energy penetrates into the skin more effectively.

In an additional construction, instead of the annular surface, the handpiece is provided with slide rails or guide rollers which facilitate manual guiding in a straight line over the skin surface. This is particularly advantageous when the laser radiation source is not switched on and off when moving from one skin area to the next, but rather the switched on laser beam is guided in a continuous, sliding manner over the skin surface. Also, the required distance of the emission surface from the skin is always ensured at the same time by means of such glide rails.

The glide rails can advantageously be constructed as filter glass disks which protect the operator from the laser radiation at the same time.

The handpiece according to the invention can also be constructed in such a way that at least one optical element with a surface which is structured in the micrometer range and is accordingly micro-optically active is provided inside the handpiece following the exit face of the beam guidance device.

This surface can have a diffractively acting structure whose width is in the order of magnitude of the wavelength of the laser beam utilized for treatment. A structure of this kind is, for example, a varying height profile with stripe-shaped, cross-shaped, funnel-shaped and/or otherwise shaped raised portions, an index of refraction varying within the above-mentioned structure width and/or varying absorption coefficients. Elements outfitted with surfaces of this type are described, for example, in Naumann, Schröder, "Baulemente der Optik [Optical Components]", Carl Hanser Verlag, Munich, Vienna, 6th edition, page 584.

By means of this microstructured surface, the energy distribution within the beam cross section is made uniform to the edge areas when the laser beam passes through this surface, i.e., a radiation intensity which is uniform over the cross section is present in the beam path following this surface over the entire beam cross section.

In an alternate construction, instead of the diffractive structure, the surface has a refractively acting structure formed, for example, of spherical, aspherical, cylindrical and/or elliptic lenses, wherein each of the lenses has a dimension vertical to the beam direction of 10 m to 1000 m. These lenses can be arranged hexagonally and/or orthogonally on the surface as an array. They can be concave dispersive lenses or convex collective lenses; concave and convex lenses can also be arranged adjacent to one another on the surface. Randomly oriented concave cutouts, notches arranged in a circle or extending helically or intersecting gratings are also conceivable.

Preferred dimensions for the refractive structures are diameters of 0.35 mm and depths of 0.005 mm. The ratio of depth to diameter should not exceed 0.5. With respect to lens structures, this ratio should be greater than 0.02 and, in particularly preferred constructions, in the range of 0.1 to 0.3.

When the laser beam passes the surface, the radiation is divided into a plurality of partial beams through the micro-optically active structure elements (lenses or height profiles), wherein the quantity of partial beams depends on the quantity of structure elements present on the surface. The finer the micro-optically active structure, the more uniform and homogeneous the distribution of the beam intensity over the entire cross section of the laser beam after passing through the described surface. In other words, when passing through the microstructured surface, an uneven energy distribution within the beam cross section is transformed into a uniform energy distribution to the edge areas of the beam cross section.

This homogenization is particularly necessary and advantageous when using a ruby laser as radiation source because, as is well known, its radiation has a highly inhomogeneous intensity distribution in cross section. In addition, the intensity distribution in the ruby laser beam is not constant, but changes from spot to spot, so that when the ruby laser is used for hair removal without the device proposed according to the invention burning can easily result.

According to the invention, not only is the intended homogenization of the intensity within the beam cross section achieved with the microstructured surface but, depending on the construction of the individual structure elements, the direction of the individual partial beams can also be influenced insofar as this is intended and desired. This means that a laser beam exiting from a fiber, e.g., with circular cross section, can be changed into a laser beam with a square, rectangular, hexagonal or otherwise shaped beam cross section by means of deliberate predetermined shaping of the individual structure elements.

This means that when square, rectangular or hexagonal beam cross sections are directed onto the skin area to be treated, the individual spots can be placed adjacent to one another without overlapping while also preventing missed untreated locations. Elimination of overlap prevents an excessive introduction of energy and elimination of untreated missed locations prevents insufficient introduction of energy, so that the treatment results are significantly improved.

The reshaping of the beam cross section is achieved in that the structure elements on the microstructured surface are selected, shaped and positioned in such a way that the partial beams are given a direction within the laser beam cross section aiming at a desired outer contour of the cross section. Accordingly, the partial beams no longer fill up a circular beam cross section, but, for example, uniformly fill up a square cross section (the circle segments are cut out).

Accordingly, compared with the prior art, the handpiece according to the invention is characterized by an intensity of the laser beam at the emission surface that is homogenized over the entire cross section and, moreover, by an adapted cross-sectional shape of the beam.

The micro-optically active structures are easily producible, for example, by means of electron beam lithography, photolithography or ion exchange methods.

In a development of the invention, a device for beam focusing is arranged in front of and behind the micro-optically structured surface. The size of the beam cross section can be adjusted with this device. For example, a collective lens can be provided as a device of this kind which is positioned in the beam path in front of or after the structured surface.

Preferably, zoom optics can be provided as a device for beam focusing; with zoom optics it is possible to influence the size of the spot in a simple manner. When the zoom optics are coupled with corresponding automatic adjustment means, the spot size can be changed during treatment in an uncomplicated manner.

In another construction of the invention, the optical element with the micro-optically active surface is constructed as a beam-guiding rod in which the beam is relayed by total reflection. The rod has an input radiation surface and an emission surface for the laser beam; the input radiation surface is provided with the micro-optically active structure. The rod can be made of silica glass. The size and cross-sectional shape can differ between the in-radiation surface and out-radiation surface. Advantageously, however, the in-radiation surface should be round, the round cross section should be retained over at least 90% of the length of the rod, and a reduction and/or change in the shape of the cross section should be provided only in the remaining length.

Because of the total reflection within the beam-guiding rod, a further "blending" of the plurality of individual partial beams present after passing through the structured surface is achieved and the beam intensity is made more uniform with respect to the beam cross section.

It should be noted that the micro-optic structures, insofar as they are formed on the in-radiation surface of a beam-guiding rod as provided according to the invention, can also be the structures of a diffusion plate or scatter disk known from the prior art. However, since the light also enters at an unfavorable angle with the indefinable structures of the scatter disk, the back reflections would result in energy losses and accordingly also in undesirably excessive heat development.

This is prevented by the micro-optically active structures because they are constructed in such a way that unfavorable entrance angles do not occur. In this case, in accordance with the Fresnel equations (relationship between polarization, reflection, absorption), approximately 96% of the laser radiation is coupled in, so that the energy loss and accordingly also the heat development is limited to a reasonable amount.

An additional influencing of the beam intensity distributed over the cross section can be achieved when the structured surface is curved, preferably in concave manner, but particularly preferably also in convex manner.

The emission surface can have a circular as well as a polygonal, e.g., square or hexagonal, cross section.

Further constructions in which a ruby laser or a laser diode integrated in the handpiece is provided as laser radiation source lie within the scope of the invention.

Further, a layer of transparent gel, for example, an ultrasound gel, can be provided between the emission surface and the skin surface to be treated. The radiating of the laser beam into the skin surface to be treated is further optimized in this way by reducing the reflection and decreasing scatter. As a further result, lower energy densities are needed for the laser light. The refractive index of the gel is to be adapted to the refractive index of the skin and the gel should be transparent at least for the wavelength of the utilized laser light.

The invention is further directed to a method for cosmetic treatment of skin surfaces while operating a handpiece corresponding to the preceding description. According to the invention, a first contact surface is initially placed on a selected skin area to be treated for purposes of moderating temperature. After a predetermined holding time during which this first contact surface is held on the skin area, the position of the handpiece is changed in such a way that the laser radiation emission surface, and not the contact surface, is located over this skin area. The contact surface is already in heat-conducting contact with another skin area to be treated which is located directly adjacent to the first skin area. During the period in which the contact surface is held on the second skin area, the treatment of the first skin area with the laser beam is carried out.

After the treatment is concluded, after which pre-cooling of the second skin area is also concluded, the position of the handpiece is changed in such a way that the exit surface for the laser beam is now located over the second skin area and the contact surface is in heat-conducting contact with a third skin area and effects a preliminary moderation of the temperature of the latter. During this holding time, the second skin area undergoes treatment with the laser radiation.

Alternatively, the change in the position of the handpiece from one treated skin area to the next can be carried out by shifting, wherein the handpiece is applied, the radiation source is switched on for the treatment period specifically for this skin area and is then switched off again, or by moving in a sliding manner over the skin areas to be treated, while the laser beam remains switched on.

In the latter case, the laser energy, the cooling temperature at the contact surface for pre-cooling, the temperature at the contact surface for subsequent temperature moderation (if any) and the forward feed speed of the handpiece are adapted to one another in such a way that treatment is carried out in an optimal manner. A plurality of "paths" of this kind can be carried out side by side to treat a larger skin surface.

In a further development of this method for cosmetic treatment of skin surfaces using the handpiece described above, a gel is applied to the skin surface to be treated before the treatment is started, wherein the gel is transparent for the wavelength of the utilized laser light and its index of refraction is adapted to the index of refraction of the skin. In this way, laser energy is effectively applied to the skin because the light reflected by the skin is reduced to an insignificant proportion. This prevents secondary effects which would otherwise occur due to lost heat.

An ultrasound gel whose index of refraction lies between that of the emission surface and that of the skin surface to be treated is preferably used. The ultrasound gel is physiologically tolerated and therefore suitable for cosmetic purposes. Moreover, it has good heat conductivity.

The gel further reduces the risk of damaging the epidermis. The efficacy of the gel can be further increased by removing any hair from the part of the skin to be treated before beginning the treatment.

BRIEF DESCRIPTION OF THE DRAWINGS

In the accompanying drawings:

FIG. 1 shows a schematic view of the arrangement according to the invention in a first construction variant;

FIG. 2 shows the laser beam cross section inside the handpiece according to FIG. 1 at various positions;

FIG. 3 shows a view A from FIG. 1;

FIG. 4 shows a schematic view of the arrangement according to the invention in a second construction variant;

FIG. 5 shows the laser beam cross section inside the handpiece according to FIG. 4 at various positions;

FIG. 6 shows a view B from FIG. 4;

FIG. 10 shows design variants of an in-radiation surface with micro-optic structure in cross section;

FIG. 11 shows design variants of an in-radiation surface with micro-optic structure in a top view; and FIG. 12 shows a micro-optic structure in cross section.

DESCRIPTION OF THE PREFERRED EMBODIMENTS

Figure 8:
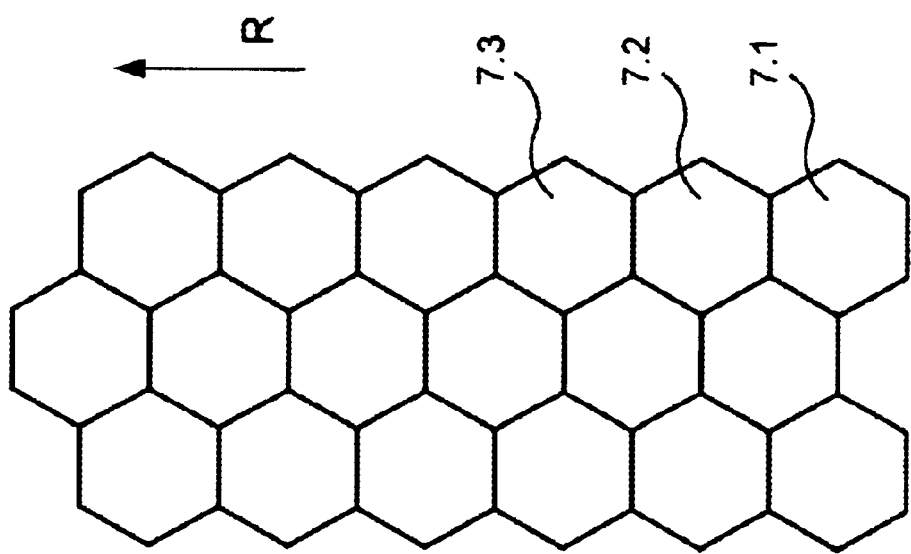
FIG. 8 shows an arrangement in series of skin areas treated with an arrangement according to FIG. 4.

FIG. 1 shows a first construction variant of the handpiece according to the invention in a schematic view. An optical element, for example, a disk 3 made of silica glass and provided with a micro-optically active surface 4, and zoom optics 5, 6 indicated by two lenses, is located in the beam path 1 of a laser beam proceeding from a radiation source and coupled into the handpiece 11 via a beam guidance device 2. The beam guidance device 2 can be constructed as a flexible light-conducting fiber or in the form of rigid transmission elements which are connected with one another by joints.

The laser beam 1 is directed onto a skin area 7.1 and accordingly onto a portion of a larger skin surface 7 to be treated, for example, for purposes of hair removal or for some other cosmetic treatment.

The surface 4 of the optical element 3 has a refractively active structure comprising a plurality of concave spherical lenses. The surface 4 is placed in the beam path 1 in such a way that the entire beam path 1 must traverse these microlenses. Each lens preferably has a diameter of approximately 0.35 mm and a preferred depth of 0.005 mm.

When the laser beam 1 passes through the microlens arrangement on the surface 4, the laser beam coming, for example, from a ruby laser is separated into a plurality of partial beams corresponding to the quantity of microlenses. As a result of this separation, the indicated circular cross section 8 of the beam path 1 which has an uneven intensity distribution is transformed into a beam with uniform intensity distribution within a square cross section 9 (see also FIG. 2). Accordingly, the disk 3 not only causes a change in the intensity distribution inside the laser beam cross section, but also, at the same time, causes a change in the cross-sectional shape of the laser beam.

With this square cross-sectional shape of the beam path 1 after passing through disk 3, the beam is directed onto the skin part 7.1, wherein the size of the cross-sectional surface 10 impinging on the skin part 7.1 can be influenced by the zoom optics 5, 6. By varying the zoom optics, the cross-sectional surface 10 impinging on the skin area 7.1 can be made larger or smaller. Accordingly, it is possible in a simple manner to adapt to the surface of the skin area to be treated. The size of the cross-sectional surface 10 is 10 mm×10 mm, for example.

In cosmetic treatments, as a rule, the area to be treated is larger as a whole than the cross-sectional area 10 that is adjustable by the zoom optics 5, 6; that is, the entire skin surface to be treated must be covered completely by a plurality of contiguous cross-sectional surfaces 10. This is achieved in that, after the treatment of the skin area 7.1, the handpiece is moved to an adjacent skin area 7.2 which is then exposed to laser radiation and is then converted to the next skin area 7.3, and so on, until the entire skin surface for which treatment was intended has been covered (see FIG. 7).

A diffractively active structure can be provided on the surface 4 as an alternative to a refractively active structure. Accordingly, a homogenization of intensity within the laser beam cross section is achieved by phase changes rather than by dividing the laser beam into a plurality of partial beams. Also, by means of the disk 3, for example, a circular beam cross section with uneven intensity distribution can be transformed into a square cross section with a uniform intensity distribution.

In order to prevent damage by laser radiation treatment, particularly to sensitive skin layers, the handpiece is outfitted with a device for moderating the temperature of the selected skin area 7.1 before and/or after treatment. Moderating the temperature of the skin area 7.1 can be effected by heating to a predetermined temperature or by cooling. However, in the following, the embodiment example will be described with reference to a cooling of the skin area 7.1.

For this purpose, the handpiece 11 is provided with a contact surface 12. The contact surface 12 corresponds with respect to its shape and dimensions to the laser beam cross section as is shown in FIG. 3. Further, a Peltier element 14 is provided inside the handpiece so as to be surrounded by a housing 13, the cool side 15 of the Peltier element 14 being in contact with a heat conductor at which the contact surface 12 is formed.

The warm side 17 of the Peltier element 14 is provided with ducts 18 through which a heat transfer medium is pumped in a circuit. The supply of heat transfer medium, e.g., water, is carried out via connections 19 which are connected with the ducts 18. When the heat transfer medium circulates, the heat energy which is transported from the cool side 15 to the warm side 17 during operation of the Peltier element 14 is guided out of the Peltier element 14. The energy supply in the form of electrical potential required for operation of the Peltier element 14 is not shown in the drawing.

During operation of the arrangement according to the invention, the contact surface 12 is initially placed on a skin area 7.1 selected for treatment. After a predetermined holding time during which the contact surface 12 is held on the skin area 7.1 and during which heat is removed from the skin area in the manner described above so that the skin area 7.1 is cooled, the position of the handpiece 11 is changed in such a way, instead of the contact surface 12, that the emission surface 20 from which the laser radiation exits from the handpiece 11 is located over the skin area 7.1.

Figure 7:
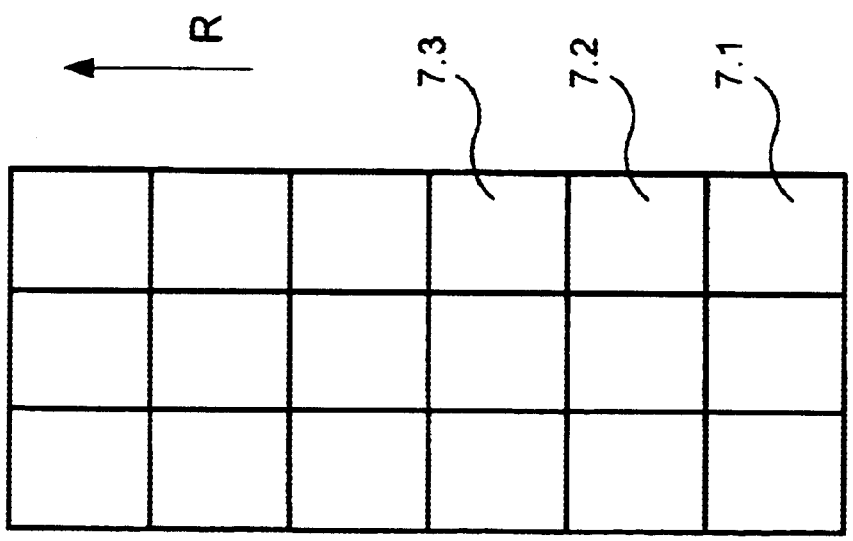
FIG. 7 shows an arrangement in series of skin areas treated with an arrangement according to FIG. 1.

At the same time, the contact surface 12 is brought into contact with another skin area 7.2 to be treated (FIG. 7). While the skin area 7.2 is cooled, the laser source is put into operation via an operator's unit which can be controlled, for example, by means of a foot switch.

After a given period during which the laser radiation acts upon the skin area 7.1, the laser source is switched off again. The position of the handpiece is now changed in such a way that the emission surface 20 is located over the second skin area 7.2, while the contact surface 12 is brought into contact with a third skin area 7.3. During the period in which the contact surface 12 is held on the third skin area 7.3, the laser source is again switched on and the treatment of the skin area 7.2 is carried out as was already described.

The entire skin surface to be treated is scanned progressively until treatment of the series of individual skin areas 7.1, 7.2, 7.3, and so on, is completed. One skin area is pre-cooled while another is treated with the laser radiation.

In a development of the invention, the handpiece 11 can be outfitted with another contact surface 26 which communicates, e.g., via a heat conductor 27 (both indicated in FIG. 1) with another cooling unit, e.g., a Peltier element, which is arranged in the handpiece 11. In this regard, it is possible to arrange the two contact surfaces 12 and 26 and cross-sectional surface 10 with which the beam path 1 impinges on the treatment area in a straight line as is shown in FIG. 3.

When the handpiece 11 is moved in direction R (see FIG. 3) from one skin area to the next during the treatment of a larger surface segment, pre-cooling is carried out initially with contact surface 12, then, after a first displacement of the handpiece 11, the pre-cooled skin area is treated by laser radiation in that the laser beam impinges on this skin area, and in the subsequent, second displacement of the handpiece 11, also again by an increment corresponding to the distance between the contact surface 12 and the cross-sectional surface 10, the skin area that has already been treated by the contact surface 26 placed on it is subjected to subsequent cooling. The subsequent temperature moderation serves primarily to protect the skin.

The temperature of the contact surface 12 and the intensity of the laser radiation are adapted to one another in such a way that the time required for pre-cooling corresponds approximately to the acting period of the laser radiation, so that an effective and progressive treatment from one skin area to the other is possible without stationary times.

If desired, this progressive treatment can also be carried out continuously with constant laser radiation in that the handpiece is guided manually over the skin in a gliding manner. In this respect, in order to achieve an at least approximately straight line forward feed movement, filter disks 28 are provided in one embodiment and are positioned lateral to the surfaces 12, 10 and 26 which are arranged in a straight line. The filter disks 28 are indicated in FIG. 1 and FIG. 3. These can also be rotatable disks which roll on the skin.

The narrow edges of the filter disks which are placed upon the skin are used by the operator as support in guiding the handpiece in a straight line from one area of the skin to another and at the same time form a protection against damaging laser radiation insofar as the filters are adapted to the wavelength of the radiation.

As was already shown, not only is the radiation intensity homogenized in relation to the cross section of the laser beam by the disk 3, but a cross-sectional shaping of the beam path 1 is also carried out. In so doing, it is possible (as was described above) not only to form a square cross section 9 from a circular cross section 8 of the beam path 1 (see FIG. 2), but it is also possible to arrange the optical element 3 in such a way that a circular cross section of the beam path 1 results at position 9 as is shown in FIG. 5.

FIG. 4 shows a second basic construction variant of the arrangement according to the invention. In this case, the beam path 1 which is likewise coupled in via a beam guidance device 2 initially also has a circular cross section 8 with inhomogeneous distribution of radiation intensity. However, in contrast to the construction variant according to FIG. 1, a collective lens 22 is placed in the beam path and focuses the laser beam on the in-radiation surface 23 of a beam-guiding rod 24.

The in-radiation surface 23 is provided with a structure of microlenses arranged next to one another (see also FIGS. 10 to 12). In this case, the laser radiation is also divided into a quantity of partial beams corresponding to the plurality of microlenses and the intensity distribution is homogenized in this way. Within the beam-guiding rod 24, the laser beam is conveyed by total reflection, wherein a further homogenization is achieved. A laser beam whose cross section has a radiation intensity which is uniform into the edge areas is available at the emission surface 25 that is positioned near the selected skin area or in immediate contact with it during treatment. This ensures a uniform treatment of the skin area acted upon by this laser radiation.

Beam shaping is carried out in this case inside the rod 24 in that the beam cross section is changed by corresponding shaping of the rod cross section from the non-circular cross section 9 of the beam before it enters the in-radiation surface 23 to a polygonal cross-sectional shape (cross section 10) of the emission surface 25. In this regard, the emission surface 25 is reduced relative to the in-radiation surface 23, wherein the circular cross section is retained over at least 90% of the length of the rod and a reduction in and/or change in shape of the cross section should be provided first on the remaining length portion.

Also, in this construction variant, the handpiece 11 is again provided with a contact surface 12 which is coupled with the cool side 15 of a Peltier element 14 via a heat conductor 16. As was already described with reference to FIG. 1, the heat energy is also carried off from the warm side 17 in this case with the assistance of a heat transfer medium circulating through ducts 18.

As in the embodiment described with reference to FIG. 1, another contact surface 26, another heat conductor 27, another cooling unit, and so on, can also be provided in this case (shown by the dashed lines). A handpiece constructed in the manner described herein can be used for the method in the same way as the handpiece according to the construction variant according to FIG. 1.

As is shown in FIG. 6, it is provided by way of example that the cross section of the emission surface 25 and the cross section of the contact surface 12 (as well as the contact surface 26) are constructed in hexagonal shape. Therefore, in a manner similar to that described above, the successively treated skin areas can be taken in succession until the entire skin area to be treated is covered without gaps (see FIG. 8).

Figure 9:
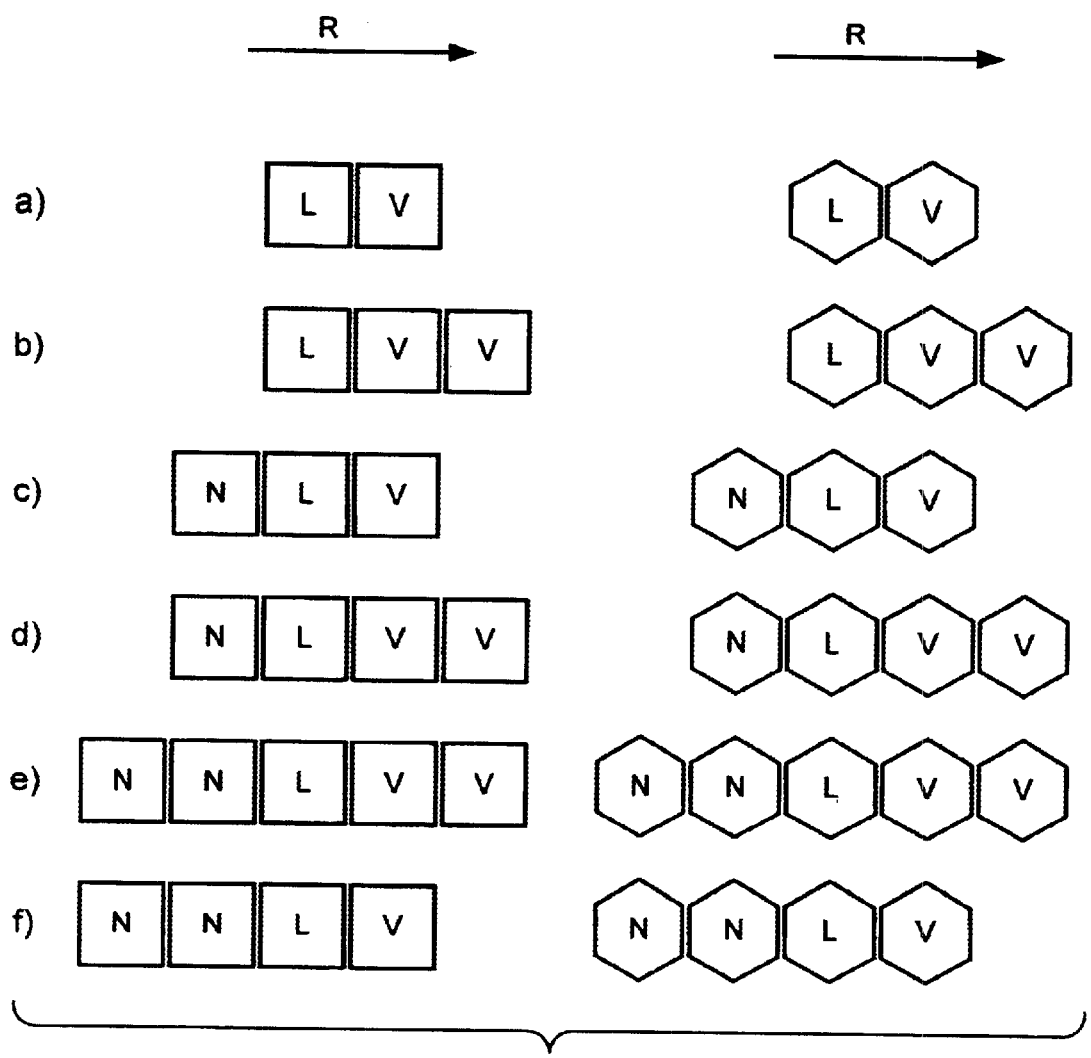
FIG. 9 shows various possibilities for adjacent skin areas which are moderated with respect to temperature beforehand, treated and then moderated with respect to temperature subsequently.

FIG. 9 shows different possible arrangements with respect to the proximity of the skin areas that are subjected to preliminary temperature control, treated and subjected to subsequent temperature control, where L represents lasers at the moment of treatment, V represents preliminary temperature control in preparation for the laser, and N represents subsequent temperature control for subsequent treatment of the skin area that has already been influenced by laser radiation. The individual surface segments can have different geometric shapes and areas whose extent varies from one to another. For the sake of simplicity, only square and hexagonal shapes of approximately equal extent are shown.

As is shown by way of example in FIG. 10, the in-radiation surface 23 can be flat (FIG. 10a), concave (FIG. 10b) or convex (FIG. 10c). Accordingly, in connection with the selection of the structure applied to the in-radiation surface 23, it is possible to deliberately influence the radiation intensity as well as the beam cross section.

FIG. 11 is a top view showing a plurality of variations in the in-radiation surfaces 4, 23. Various micro-optically active structures are shown, likewise by way of example, not in scale, but substantially magnified for the sake of clarity. FIG. 11a shows the arrangement of a plurality of lens-like depressions which are randomly distributed over the entire in-radiation surface 23.

In FIG. 11b, the structure is formed of centrally arranged grooves, each having a wedge-shaped cross section. A cross section of this kind is shown by way of example in FIG. 12. In FIG. 11c, a microstructure comprising a spiral-shaped groove is provided. FIG. 11d, on the other hand, shows a network of intersecting straight lines which can likewise have the cross section according to FIG. 12.

While the foregoing description and drawings represent the present invention, it will be obvious to those skilled in the art that various changes may be made therein without departing from the true spirit and scope of the present invention.

What is claimed is:

1. A dermatological handpiece by which a laser beam is directed to the surface of a selected skin area, wherein the skin area is subjected to an action of the laser beam, and wherein the laser beam is directed successively to individual skin areas corresponding to a laser beam cross section and covering the selected skin area in its entirety, outfitted with a device for moderating the temperature of the skin area at the surface of the skin area, comprising:

a dermatological handpiece with a guide for a laser beam:
at least one temperature-moderated contact surface which is positioned laterally adjacent to the laser beam directed onto a skin area and whose shape and area dimensions correspond approximately to the shape and area dimensions of the laser beam cross section; and wherein a distance between the laser beam and contact surface being dimensioned in such a way that a first skin area which was treated previously and/or a third skin area to be treated subsequently are/is in contact with the at least one temperature-moderated contact surface at the same time that the laser beam acts upon the selected skin area; and at least one optical element for changing the intensity distribution within the cross-sectional surface or for changing the cross-sectional surface with respect to shape or dimensions wherein a temperature sensor is provided for detecting a temperature at the contact surface and/or the selected skin area, wherein a signal output of the temperature sensor is connected with a threshold switch, by which a switch-on signal is sent to the cooling and/or heating unit as soon as a pre-adjusted temperature value is not reached or is exceeded and;

wherein, further, the switch-on signal of a threshold switch contacts a signal transmitter by which a perceptible acoustic signal is sent to a signal transmitter as soon as a pre-adjusted temperature value is not reached or is exceeded.

2. The dermatological handpiece according to claim 1, wherein there is at least one cooled contact surface.

3. The dermatological handpiece according to claim 1, wherein the contact surface is dimensioned so as to be greater than the cross-sectional surface of the laser beam by a factor of 1.1 to 2.

4. The dermatological handpiece according to claim 3, wherein the contact surface is dimensioned so as to be greater than the cross section surface of the laser beam by a factor of 1.2.

5. The dermatological handpiece according to claim 1, wherein the contact surface is dimensioned so as to be smaller than the cross-sectional surface of the laser beam by a factor of 0.9 to 0.5.

6. The dermatological handpiece according to claim 5, wherein the contact surface is dimensioned so as to be smaller than the cross-sectional surface of the laser beam by a factor of 0.7.

7. The dermatological handpiece according to claim 1 wherein a device for temperature moderation has a cooling unit and/or heating unit which communicates in a heat-conducting manner with the at least one temperature-moderated contact surface, preferably of a heat transfer medium circulating in a circuit.

8. The dermatological handpiece according to claim 7, wherein a Peltier element whose cool side communicates in a heat-conducting manner with the contact surface and whose warm side is connected with a cooling circulation is provided as cooling unit.

9. The dermatological handpiece according to claim 7, wherein the contact surface communicates in a heat-conducting manner with an expanding, and therefore cooling, gas.

10. The dermatological handpiece according to claim 9, wherein the cooling gas is preferably $N_2$.

11. The dermatological handpiece according to claim 1, wherein at least two contact surfaces are provided whose centers lie on a straight line with the center of a cross-sectional surface, wherein the distance between the centers of the cross-sectional surface and one of the contact surfaces corresponds approximately to the distance between two directly adjoinig skin areas.

12. The dermatological handpiece according to claim 11, wherein the laser beam exits between the two contact surfaces.

13. The dermatological handpiece according to claim 1, wherein a device for beam focusing, a collective lens, is arranged in front of or behind an optical element.

14. A dermatological handpiece by which a laser beam is directed to the surface of a selected skin area, wherein the skin area is subjected to an action of the laser beam, and wherein the laser beam is directed successively to individual skin areas corresponding to a laser beam cross section and covering the selected skin area in its entirety, outfitted with a device for moderating the temperature of the skin area at the surface of the skin area, comprising:
 a dermatological handpiece with a guide for a laser beam;
 at least one temperature-moderated contact surface which is positioned laterally adjacent to the laser beam directed onto a skin area and whose shape and area dimensions correspond approximately to the shape and area dimensions of the laser beam cross section, and wherein a distance between the laser beam and contact surface being dimensioned in such a way that a first skin area which was treated previously and/or a third skin area to be treated subsequently are/is in contact with the at least one temperature-moderated contact surface at the same time that the laser beam acts upon the selected skin area;
 at least one optical element for changing the intensity distribution within the cross-sectional surface or for changing the cross-sectional surface with respect to shape or dimensions,
 wherein at least one optical element with an in-radiation surface which is sized in a micrometer scale and is accordingly micro-optically diffractive or refractive is provided;
 wherein the in-radiation surface has a diffractively active structure in which the structure width corresponds approximately to a wavelength of a laser radiation used for a treatment and which is constructed as a varying height profile selected from the group consisting of stripe-shaped, cross-shaped, funnel-shaped and shaped raised portions, as a varying index of refraction or in the form of a varying absorption coefficient.

15. The dermatological handpiece according to claim 14, wherein the in-radiation surface has a refractively acting structure formed of a profile selected from the group consisting of spherical, aspherical, cylindrical and elliptic lenses arranged hexagonally or orthogonally and having a concave or convex shape.

16. The dermatological handpiece according to claim 14, wherein the optical element is constructed as a beam-guiding rod having a refractively structured in-radiation surface in which the beam is sent by total reflection and is radiated onto a skin surface from an emission surface.

17. The dermatological handpiece according to claim 16, wherein the in-radiation surface is curved.

18. The dermatological handpiece according to claim 17, wherein the in-radiation surface is concave in shape.

19. The dermatological handpiece according to claim 17, wherein in-radiation surface is convex in shape.

20. The dermatological handpiece according to claim 16, wherein the emission surface has a circular cross section.

21. The dermatological handpiece according to claim 16, wherein the emission surface has a polygonal cross section.

22. The dermatological handpiece according to claim 16, wherein the emission surface has a square cross section.

23. The dermatological handpiece according to claim 16, wherein the emission surface has a hexagonal cross section.

24. A method for cosmetic treatment of skin,
 wherein a dermatological handpiece by which a laser beam is directed to the surface of a selected skin area, wherein the skin area is subjected to an action of the laser beam, and wherein the laser beam is directed successively to individual skin areas corresponding to a laser beam cross section and covering the selected skin area in its entirety, outfitted with a device for moderating the temperature of the skin area at the surface of the skin area, comprising:
 providing a dermatological handpiece with a guide for a laser beam;
 providing at least one temperature-moderated contact surface which is positioned laterally adjacent to the laser beam directed onto a skin area and whose shape and area dimensions correspond approximately to the shape and area dimensions of the laser beam cross section; and wherein a distance between the laser beam and contact surface being dimensioned in such a way that a first skin area which was treated previously and/or a third skin area to be treated subsequently are/is in contact with the at least one temperature-moderated contact surface at the same time that the laser beam acts upon the selected skin area;
 providing at least one optical element for changing the intensity distribution within the cross-sectional surface or for changing the cross-sectional surface with respect to shape or dimensions;
 initially placing a contact surface on a first skin area for purposes of moderating temperature;
 holding the contact surface on this skin area a predetermined holding time;
 changing the orientation of the handpiece in such a way that a laser radiation emission surface, and not the contact surface, is now located over the first skin area;
 while the contact surface is already in contact with a second skin area, carrying out a treatment of the first skin area with the laser beam;
 changing the orientation of the handpiece in such a way that an emission surface is now located over the second skin area;
 while the contact surface is already in contact with a third skin area, carrying out the treatment of the second skin area
 wherein a medium is applied to an emission surface and/or to a skin surface before the treatment is started, wherein the medium reduces the reflection of laser radiation from a skin surface so that an energy enters the skin more efficiently.

25. The method for cosmetic treatment of skin surfaces according to claim 24, wherein the handpiece is lifted from a skin area and moved to a next skin area, wherein the laser beam is switched off and then on again.

26. The method for cosmetic treatment of skin surfaces according to claim 24, wherein the handpiece is displaced in a sliding manner with continuous laser radiation and a laser radiation is introduced successively in the skin areas.

27. The method according to claim 24, wherein the medium is an ultrasound gel.

28. The method for cosmetic treatment of skin surfaces according to claim 24, wherein a layer of a medium which is transparent for laser radiation is provided between a emission surface and a skin surface.

29. The method for cosmetic treatment of skin surfaces according to claim 28, wherein the medium layer is a gel.

30. The method for cosmetic treatment of skin surfaces according to claim 29, wherein the medium layer is an ultrasound gel.

31. The method for cosmetic treatment of skin surfaces according to claim 30, wherein the ultrasound gel is applied to a skin surface up to a maximum thickness of 1 mm.

32. A dermatological handpiece by which a laser beam is directed to the surface of a selected skin area, wherein the skin area is subjected to an action of the laser beam, and wherein the laser beam is directed successively to individual skin areas corresponding to a laser beam cross section and covering the selected skin area in its entirety, outfitted with a device for moderating the temperature of the skin area at the surface of the skin area, comprising:

at least one temperature-moderated contact surface which is positioned laterally adjacent to the laser beam directed onto a skin area and whose shape and area dimensions correspond approximately to the shape and area dimensions of the laser beam cross section;

distance between the laser beam and contact surface being dimensioned in such a way that a first skin area which was treated previously and/or a third skin area to be treated subsequently are/is in contact with the at least one temperature-moderated contact surface at the same time that the laser beam acts upon the selected skin area;

wherein a temperature sensor is provided for detecting a temperature at the contact surface and/or the selected skin area, wherein a signal output of the temperature sensor is connected with a threshold switch, by which a switch-on signal is sent to the cooling and/or heating unit as soon as a pre-adjusted temperature value is not reached or is exceeded; and wherein, further, the switch-on signal of a threshold switch contacts a signal transmitter by which a perceptible acoustic signal is sent to a signal transmitter as soon as a pre-adjusted temperature value is not reached or is exceeded.

33. A method for cosmetic treatment of skin surfaces using a dermatological handpiece by which a laser beam is directed to the surface of a selected skin area, wherein the skin area is subjected to an action of the laser beam, and wherein the laser beam is directed successively to individual skin areas corresponding to a laser beam cross section and covering the selected skin area in its entirety, outfitted with a device for moderating the temperature of the skin area at the surface of the skin area, comprising:

positioning at least one temperature-moderated contact surface which is positioned laterally adjacent to the laser beam directed onto a skin area and whose shape and area dimensions correspond approximately to the shape and area dimensions of the laser beam cross section;

dimensioning a distance between the laser beam and contact surface in such a way that a first skin area which was treated previously and/or a third skin area to be treated subsequently are/is in contact with the at least one temperature-moderated contact surface at the same time that the laser beam acts upon the selected skin area;

providing at least one optical element for changing the intensity distribution within the cross-sectional surface or for changing the cross-sectional surface with respect to shape or dimensions;

providing at least one optical element with an in-radiation surface which is sized in a micrometer scale and is accordingly micro-optically diffractive or refractive and wherein the in-radiation surface has a diffractively active structure in which the structure width corresponds approximately to a wavelength of a laser radiation used for a treatment and which is constructed as a varying height profile selected from the group consisting of stripe-shaped, cross-shaped, funnel-shaped and shaped raised portions, as a varying index of refraction or in the form of a varying absorption coefficient.

34. A dermatological handpiece by which a laser beam is directed to the surface of a selected skin area, wherein the skin area is subjected to an action of the laser beam, and wherein the laser beam is directed successively to individual skin areas corresponding to a laser beam cross section and covering the selected skin area in its entirety, outfitted with a device for moderating the temperature of the skin area at the surface of the skin area, comprising:

at least one temperature-moderated contact surface which is positioned laterally adjacent to the laser beam directed onto a skin area and whose shape and area dimensions correspond approximately to the shape and area dimensions of the laser beam cross section;

distance between the laser beam and contact surface being dimensioned in such a way that a first skin area which was treated previously and/or a third skin area to be treated subsequently are/is in contact with the at least one temperature-moderated contact surface at the same time that the laser beam acts upon the selected skin area;

initially placing a contact surface on a first skin area for purposes of moderating temperature;

holding the contact surface on this skin area a predetermined holding time;

changing the orientation of the handpiece in such a way that a laser radiation emission surface, and not the contact surface, is now located over the first skin area;

while the contact surface is already in contact with a second skin area, carrying out a treatment of the first skin area with the laser beam;

changing the orientation of the handpiece in such a way that a emission surface is now located over the second skin area;

while the contact surface is already in contact with a third skin area, carrying out the treatment of the second skin area; and wherein a medium is applied to an emission surface and/or to a skin surface before the treatment is started, wherein this gel reduces the reflection of laser radiation from a skin surface so that an energy enters the skin more efficiently wherein the medium is an ultrasound gel.

* * * * *